United States Patent [19]

Mondron

[11] 3,980,706

[45] Sept. 14, 1976

[54] SYNTHESIS OF 2,7-BISDIMETHYLAMINO-10-P-DIMETHYLAMINOPHENYL-9,10-DIHYDRO-9,9-DIMETHYLANTHRACENE

[75] Inventor: Peter J. Mondron, Cleveland, Ohio

[73] Assignee: Horizons Incorporated a division of Horizons Research Incorporated, Cleveland, Ohio

[22] Filed: Nov. 6, 1975

[21] Appl. No.: 629,236

[52] U.S. Cl. .............................. 260/576; 260/618 B
[51] Int. Cl.² .............................. C07C 85/24
[58] Field of Search .............................. 260/576, 618 B

[56] References Cited

UNITED STATES PATENTS

| | | | |
|---|---|---|---|
| 3,342,595 | 9/1967 | Sprague et al. | 96/90 R |
| 3,660,096 | 5/1972 | Wainer et al. | 96/90 R |

*Primary Examiner*—Allen B. Curtis
*Attorney, Agent, or Firm*—Lawrence I. Field

[57] ABSTRACT

The preparation of leucodihydroanthracenes represented by the general formula

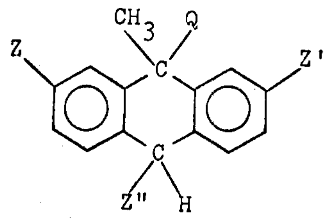

wherein each of Z and Z′ is selected from the group consisting of H and dialkylamino, and at least one Z is dialkylamino and each Q is selected from the group consisting of H and alkyl ($C_1$–$C_4$) and Z″ is selected from the group consisting of aryl, alkyl and H, the preferred Z″ being

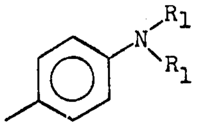

.

3 Claims, No Drawings

SYNTHESIS OF 2,7-BISDIMETHYLAMINO-10-P-DIMETHYLAMINOPHENYL-9,10-DIHYDRO-9,9-DIMETHYLANTHRACENE

This invention relates to the preparation of leuco dihydroanthracenes represented by the general formula

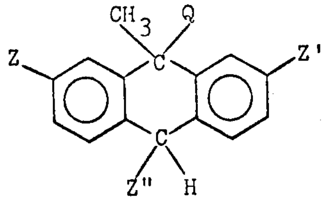

in which Q represents H or alkyl; Z and Z′ are each either H or dialkylaminos at least one of Z and Z′ being dialkylamino and Z″ represents H, alkyl or aryl including substituted aryl, particularly

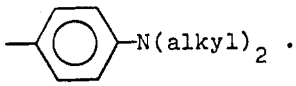 .

More particularly, this invention relates to an improved synthesis of 2,7-bisdimethylamino-10-p-dimethylaminophenyl-9,10-dihydro-9,9-dimethylanthracene, and other closely related compounds which are used in novel photographic imaging systems, e.g., as described in U.S. Pat. No. 3,342,595 issued Sept. 19, 1967 and in U.S. Pat. No. 3,660,096 issued May 2, 1972.

One method of preparation reported in the literature comprises:

1. reacting Michler's hydrol with 2-m-dimethylaminophenylpropene in 2-N-HCl, followed by neutralization and isolation of the base; and then
2. reacting the isolated product in concentrated $H_2SO_4$ to effect ring closure, followed by neutralization and isolation of the base.

This method is long and time consuming and the yield is low, especially if highly pure material is required, as is true for use in the non-silver photosensitive compositions described in the above noted patent.

The present invention is directed to improvements in the synthesis of 9,10-dihydro-anthracenes and closely related compounds. For purposes of illustration, the present invention will be described as it applies to the preparation of 2,7-bisdimethylamino-10-p-dimethylaminophenyl-9,10-dihydro-9,9-dimethylanthracene, but it is to be understood that other substituted 9,10-dihydroanthracenes may be prepared in similar fashion by choice of suitable starting materials.

In the present invention the anthracene forming reaction is carried out under conditions such that the triphenylmethane intermediate is not isolated and the ring closure to form the anthracene is carried out directly. This has the advantage of saving considerable time and effort and eliminates the need for isolation and purification of the intermediate compound.

The reaction scheme may be generally represented as follows:

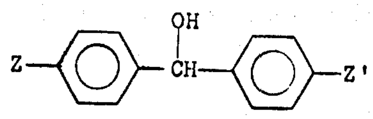

(I)

wherein each Z is either H or dialkylamino and at least one Z′ is dialkylamino preferably dimethylamino,

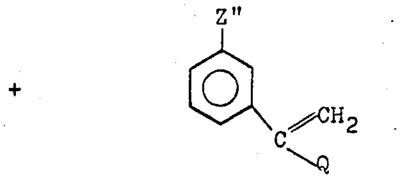

(II)

wherein Z″ represents H or dialkylamino preferably dimethylamino and Q represents alkyl, preferably methyl

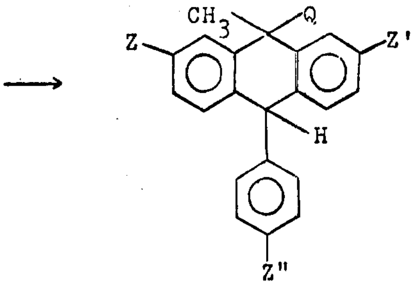

(III)

The following example, given by way of illustration of a preferred embodiment describes the preparation of 2,7-bisdimethylamino-10-p-dimethylaminophenyl-9,10-dihydro-9,9-dimethylanthracene.

25 grams of Michler's hydrol and 17 grams of 2-m-dimethylaminophenylpropene are added to 200 milliliters of stirred glacial acetic acid. The solution is stirred for one-half hour and then poured into 500 milliliters of stirred concentrated $H_2SO_4$ which is cooled in an ice bath. This solution is stirred for ½ hour and then poured into an aqueous NaOH solution containing cracked ice. The pale blue free base is then filtered and washed with water, then washed with methanol and then dried. Yield, 95%.

The compound is purified by column chromatography using activated basic alumina and eluting with 95:5 benzeneethylacetate. The solvent is removed by vacuum leaving a white solid. The white solid is then triturated with boiling hexane and then filtered and dried, giving an 85% overall yield of highly pure product.

The above Example was repeated except that the Michler's hydrol was replaced by the diethylamino anologue

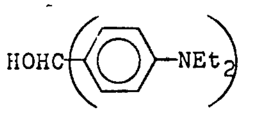 .

In the resultant product Z is dimethylamino and each of Z′ and Z″ is diethylamino. The yields were about 70% (crude) and 87% (purified) or 60% (overall).

I claim:

1. A method for synthesizing a 2,7-bis-alkylamine-9,10-dihydro-9,9-dialkylanthracene represented by the general formula:

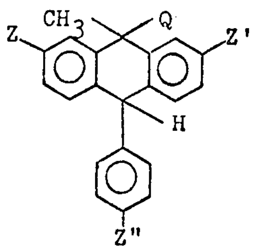

which comprises reacting:

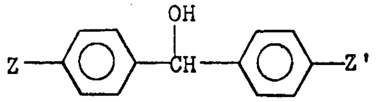

wherein Z and Z' are each selected from the group consisting of H and dialkylamino and at least one of Z and Z' is a dialkylamino group; with

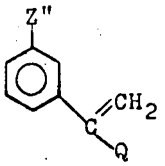

wherein Z'' is selected from the group consisting of H and dialkylamino; Q represents an alkyl group, and thereafter pouring the reacted mixture into concentrated sulfuric acid, maintained at the temperature of melting ice;

then neutralizing the resulting product with a mixture of alkali and cracked ice; and recovering the resulting anthracene.

2. The method of claim 1 including in addition purifying the resulting anthracene.

3. The process of claim 1 wherein each of Z, Z' and Z'' is dimethylamino.

* * * * *